United States Patent
Irion et al.

(10) Patent No.: US 6,860,879 B2
(45) Date of Patent: Mar. 1, 2005

(54) USE OF 5-AMINOLEVULINIC ACID OR A DERIVATE THEREOF FOR PHOTODYNAMIC DIAGNOSIS AND/OR PHOTODYNAMIC THERAPY

(75) Inventors: Klaus M. Irion, Liptingen (DE); Rainer Hahn, Tübingen (DE)

(73) Assignee: Karl Storz GmbH & Co. KG (DE)

(*) Notice: Subject to any disclaimer, the term of this patent is extended or adjusted under 35 U.S.C. 154(b) by 98 days.

(21) Appl. No.: 09/741,204

(22) Filed: Dec. 19, 2000

(65) Prior Publication Data

US 2001/0016760 A1 Aug. 23, 2001

Related U.S. Application Data

(63) Continuation of application No. PCT/EP99/04242, filed on Jun. 18, 1999.

(30) Foreign Application Priority Data

Jun. 19, 1998 (DE) .......................................... 198 27 417

(51) Int. Cl.[7] .............................................. A61B 18/18
(52) U.S. Cl. ............................. 606/16; 606/13; 606/17; 607/88; 433/25; 433/29; 433/119
(58) Field of Search ......................... 606/9–20; 433/25, 433/29–32, 118, 119; 607/88, 89

(56) References Cited

U.S. PATENT DOCUMENTS

| 3,667,454 A | 6/1972 | Prince |
| 4,184,196 A | 1/1980 | Moret et al. |
| 4,685,596 A | 8/1987 | Mattheis |

(List continued on next page.)

FOREIGN PATENT DOCUMENTS

| CA | 983900 | 2/1976 |
| DE | 27 25 793 | 6/1976 |
| DE | G85 17 634.6 | 6/1985 |

(List continued on next page.)

OTHER PUBLICATIONS

Leunig et al. Fluorescence Imaging and Spectroscopy of 5–Aminolevulinic Acid Induced Protoporphyrin IX for the Detection of Neoplastic Lesions in Oral Cavity The American Journal of Surgery, vol. 172, Dec. 1996.*

Leunig et al. Fluorescence Imaging and Spectroscopy of 5–Aminolevulinic Acid Induced Protoporphyrin IX for the Detection of Neoplastic Lesions in Oral Cavity The American Journal of Surgery, vol. 172, Dec. 1996.*

Dr. M. Kriegmair and Prof. Dr. A. Hofstetter; Photodynamische Diagnose (PDD) zur Fruherkennung des Harnblasenkarzinoms; dated 1997; 8 pages.

(List continued on next page.)

*Primary Examiner*—Linda C. M. Dvorak
*Assistant Examiner*—Ahmed M. Farah
(74) *Attorney, Agent, or Firm*—St. Onge Steward Johnston & Reens, LLC

(57) ABSTRACT

A light application unit for a combined photodynamic diagnosis and photodynamic therapy of non-malignant diseases of a parodontium and a tooth of a living being having administered a pharmaceutical preparation allowing the photodynamic diagnosis and the photodynamic therapy comprises a light source, a focusing unit for focusing light emitted by the light source, at least one element arrangeable in a light beam path of the light, and at least one wave guide for transmitting the light from the light source to a distal emitting end, the wave guide is configured rigidly in at least a distal handling end section thereof and being curved in a distal end section.

32 Claims, 4 Drawing Sheets

U.S. PATENT DOCUMENTS

| | | | |
|---|---|---|---|
| 5,079,262 A | | 1/1992 | Kennedy et al. |
| 5,098,291 A | | 3/1992 | Curtis et al. |
| 5,104,392 A | * | 4/1992 | Kittrell et al. ............... 606/15 |
| 5,388,987 A | * | 2/1995 | Badoz et al. ................ 433/29 |
| 5,388,988 A | * | 2/1995 | Goisser et al. ............... 433/29 |
| 5,409,376 A | * | 4/1995 | Murphy ..................... 433/29 |
| 5,422,093 A | | 6/1995 | Kennedy et al. |
| 5,558,518 A | | 9/1996 | Bab et al. |
| 5,570,182 A | * | 10/1996 | Nathel et al. ............... 356/345 |
| 5,620,700 A | | 4/1997 | Berggren et al. |
| 5,897,321 A | * | 4/1999 | Goodman et al. .......... 433/215 |
| 6,212,425 B1 | * | 4/2001 | Irion et al. .................. 600/476 |
| 6,270,342 B1 | * | 8/2001 | Neuberger et al. ........... 433/29 |
| 6,350,123 B1 | * | 2/2002 | Rizoiu et al. ................ 433/80 |
| 6,510,338 B1 | * | 1/2003 | Irion et al. .................. 600/476 |

FOREIGN PATENT DOCUMENTS

| | | |
|---|---|---|
| DE | 689 06 167 | 1/1989 |
| DE | 297 05 934 | 3/1997 |
| EP | 0 049 905 | 10/1981 |
| EP | 0 300 277 | 1/1989 |
| EP | 0 743 029 | 4/1996 |
| EP | 0 774 235 | 11/1996 |
| FR | 1171206 | 4/1957 |
| JP | 04299998 | 10/1992 |
| JP | 10-033576 | 2/1998 |
| WO | WO 93/21992 | 4/1993 |
| WO | WO 94/17797 | 2/1994 |
| WO | WO 95/10243 | 10/1994 |
| WO | WO95/07077 | 3/1995 |
| WO | WO 96/39188 | 6/1996 |
| WO | WO 98/10711 | 9/1996 |
| WO | WO 98/06456 | 6/1997 |
| WO | WO 98/09155 | 8/1997 |
| WO | WO/98/30242 | 1/1998 |

OTHER PUBLICATIONS

Dr. M. Kriegmair and Prof. Dr. A. Hofstetter; Photodynamic Diagnosis (PDD) for early recognition of carcinomata of the bladder; dated 1998; 12 pages.

Andreas Leunig, MD, et. al.; Fluorescence Imaging and Spectroscopy of 5–Aminolevulinic Acid Induced Protoporphyrin IX for the Detection of Neoplastic Lesions in the Oral Cavity; dated1996; 4 pages.

A. Leunig, et. al.; (XP–002078605) Photodynamische Diagnostik von Neoplasien der Mundhole nach lokaler Applikation von 5–Aminolavulinsaure; dated 1996; 6 pages.

M. Messmann, et. al.; (XP–002120197) Photodynamische Diagnostik gastrointestinaler Prakanzerosen nach Sensibilisierung mit 5–Aminolavulinsaure; dated 1998; 7 pages.

Jennifer M. Roper, et. al.; (XP–002120198) Tetrapyrrole biosynthesis in several haem–dependent anaerobic pathogens; dated 1997; 5 pages.

R. Baumgartner, et. al.; (XP–002120199); Inhalation of 5–aminolevulinic acid: a new technique for florescence detection of early stage of lung cancer; dated 1996; 6 pages.

John Weber, et. al.; (XP–0020200) On–line fluorescence of human tissues after oral administration of 5–aminoevulinic acid; dated 1997; 6 pages.

Olan Peng, et. al.; (XP–002120201) 5–Aminoevulinic Acid–Based Photodynamic Therapy; dated 1997; 27 pages.

G. Ackermann et. al.; (XP–002120202) Simulations on the selectivity of 5–aminoevulinic acid–induced florescence in vivo; dated 1998; 8 pages.

Grant et. al.; (XP–0021321811); Photodynamic therapy of oral cancer: photosensitisation with systemic aminolaevulinic acid ; dated Jul. 17, 1993 1 page.

Prokhonchukov, et. al.; (XP–0021321812) Treat Disease irradiate inflammation zone lazer beam follow surgical Aug. 23, 1994 (Enlgish abstract).

Mashchenko, et. al. (XP–002132813) Treat periodontal introducing fibre sorption pretreatment solution Root canal helium neon lazer irradiate root project dated 1994 1 page (English abstract).

Lenuig, et. al. (XP–002120196); Photodynamische Diagnostik von Neoplasien der Mundhohle nach lokaler Applikation von 5–Aminolavulinsaure; dated 1996; 6 pages.

* cited by examiner

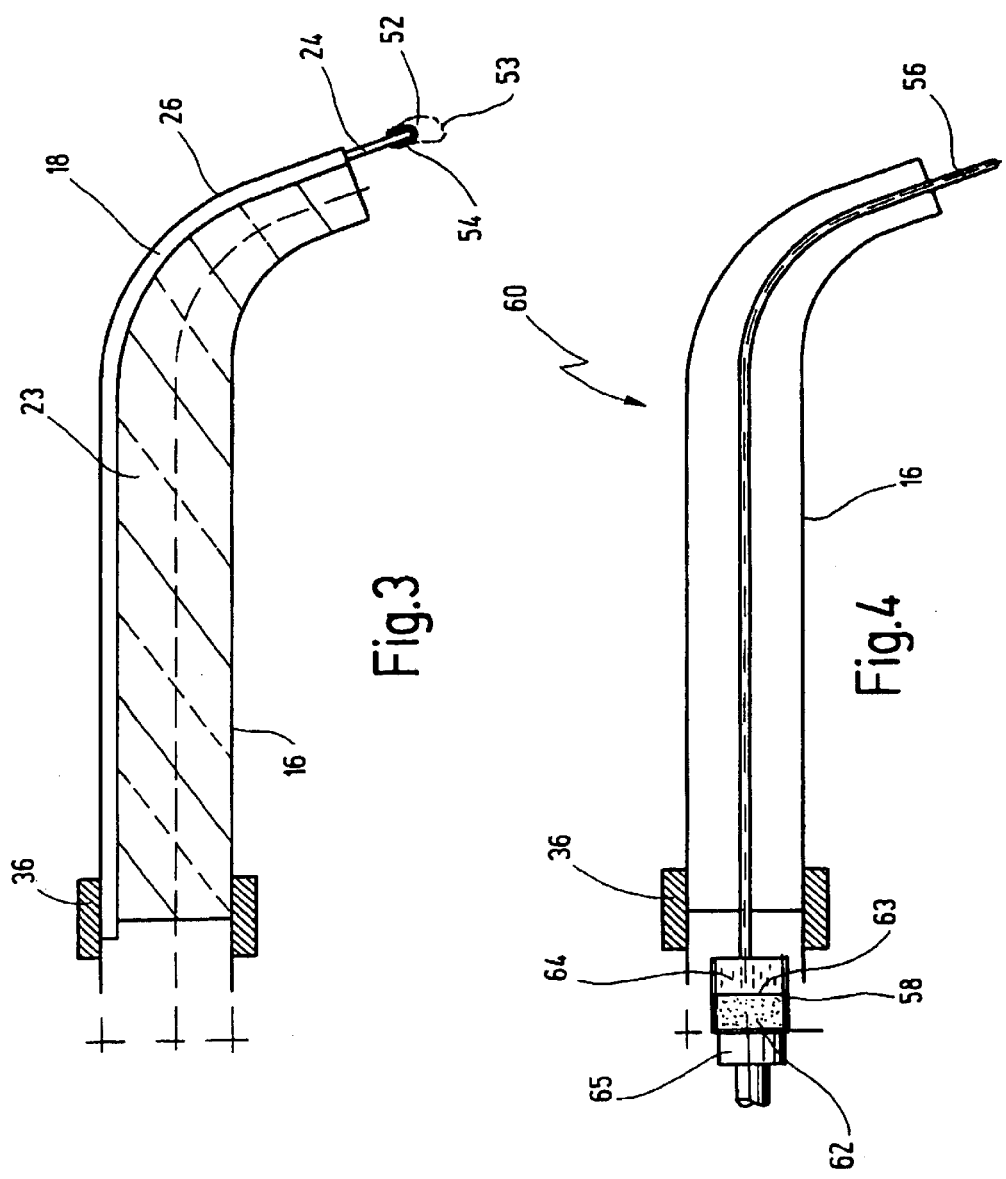

USE OF 5-AMINOLEVULINIC ACID OR A DERIVATE THEREOF FOR PHOTODYNAMIC DIAGNOSIS AND/OR PHOTODYNAMIC THERAPY

This is a continuation of pending International Application PCT/EP99/04242 filed on Jun. 18, 1999 which designates the U.S.

BACKGROUND OF THE INVENTION

The invention relates to a light application unit for combined photodynamic diagnosis (PDD) and/or photodynamic therapy (PDT) of diseases of the parodontium and the teeth.

The invention further relates to the use of 5-amino levulinic acid or a derivative thereof for producing a pharmaceutical preparation for photodynamic diagnosis and/or photodynamic therapy of diseases of the parodontium and the teeth.

The invention still further relates to an apparatus for applying the pharmaceutical preparation to the parodontium.

The use of 5-amino levulinic acid for photodynamic diagnosis (PDD) for the detection of bladder carcinoma is known from the article "Endo World" URO No. 17/1-D, 1997 of Karl Storz GmbH & Co., Tuttlingen, Germany and Karl Storz Endoscopy, USA. As is disclosed there, certain photo-sensitizers together with a special light can be used to detect malignant or other types of tissue (photodynamic diagnosis, PDD) and to destroy such tissue (photodynamic therapy, PDT). The phenomenon is observed in malignant tissue, healthy tissue does not show this phenomenon.

This phenomenon is based on the properties of 5-amino levulinic acid and consequently the induced formation of photo-sensitive protoporphyrine IX (PPIX). 5-amino levulinic acid is a precursor of the photo-sensitizer protoporphyrine IX, so that the amount of protoporphyrine IX is increased by administration of this precursor. The precursor does not become enriched and transform into PPIX in healthy tissue.

The precursor to the photo-sensitizer is applied by installation, flushing, inhalation, orally or topically. This tissue can be excited to become fluorescent with a corresponding light application system and this fluorescence is observed, which makes possible the photodynamic diagnosis (PDD). Furthermore it has been found that a photo-toxic effect occurs induced by PPIX, which opens up the possibility of photodynamic therapy (PDT).

The German patent applications DE 197 21 454 and DE 196 39 653 disclose apparatus for photodynamic diagnosis using fluorescence induced by 5-amino levulinic acid in biological tissue in vivo.

The object of the present invention is to expand the utilization of 5-amino levulinic acid and optionally derivatives thereof and to provide the corresponding apparatus.

SUMMARY OF THE INVENTION

According to the present invention, the object is achieved in that 5-amino levulinic acid or a derivative thereof is used for preparing a pharmaceutical preparation for photodynamic diagnosis and/or photodynamic therapy of non-malignant diseases of the parodontium (tooth support system) and the teeth.

The object is further achieved with a light application unit for combined photodynamic diagnosis and/or photodynamic therapy of non-malignant diseases of the parodontium and the teeth making use of such pharmaceutical preparations.

The application unit comprises a light source for generating light at least in the visible region, a focusing unit for focusing the light and at least one wave guide for transmitting the light from the light source to a distal, emitting end of the wave guide. The application unit further comprises at least one element disposed in the light beam with which the spectral properties of the light source can be altered. The wave guide is formed to be rigid at least in a distal region for handling and comprises a curved section at the distal end section.

An apparatus for applying the pharmaceutical preparation comprises at least two chambers, one chamber containing the 5-amino levulinic acid or a derivative thereof and the other second chamber a carrier substance for the compounds contained in the first chamber. Further, a mechanism is provided for connecting the two chambers and mixing the compounds contained in the two chambers shortly before application. A canula is also provided for supplying the so-formed pharmaceutical preparation to a tissue region of the parodontium or to the teeth.

Dental diseases, such as caries or parodontopathies, represent some of the most widely known diseases. Current treatment methods of parodontitis are based on the one hand on an instrumental, purely mechanical or ultrasound cleaning of the gums or the edges of the gums or the surface of the teeth or pockets in the gums. On the other hand, methods are used based on washing or purging the inflamed tissue with anti-bacterial chemical substances, with the purpose of destroying the bacteria which cause the inflammation.

Affected or non-affected tissue areas are sometimes only difficult to differentiate. For serious inflammation or rapidly developing parodontopathies, a high systemic dosis of antibiotics is the only possibility of containing the disease, because the deeper lying bacteria in the parodontal soft tissue cannot be or only be partially inactivated by mechanical or ultrasound cleaning and flushing. Such antibiotic treatment however have a number of side effects, i.e. destruction of the intestinal flora or development of resistance, so that these therapies are not satisfactory.

Caries are also caused by bacteria, mostly as the consequence of tooth demineralization from monosaccharides.

It has now surprisingly been found that both a photodynamic diagnosis and a photodynamic therapy of non-malignant diseases of the parodontium or the teeth can be carried out successfully using 5-amino levulinic acid or derivatives thereof. This is surprising because a number of different agents or germs are responsible for diseases of the parodontium or the teeth. Even so, a reliable photodynamic diagnosis can be carried out using 5-amino levulinic acid or derivatives thereof and of even greater significance, a successful photodynamic therapy can be carried out.

By configuring the light application unit with the above-mentioned features, the light can be directly applied to the parodontium or the teeth via the curved distal section of the wave guide, in particular also to the gum pockets between the gums and the teeth which arise in such diseases of the parodontium.

The 5-amino levulinic acid or derivatives thereof can be applied, as is known, orally, parenteral, systemic, however also topically, where the gum pockets can be used to apply the pharmaceutical preparation. Namely, the preparation can remain there, so that the 5-amino levulinic acid or its derivatives can penetrate into the corresponding regions of the tissue. The apparatus for application thus comprises a suitable canula for this purpose.

In further embodiments of the present invention, the 5-amino levulinic acid or one of its derivatives is used for producing a pharmaceutical preparation for photodynamic diagnosis and/or photodynamic therapy of parodontitis, parodontopathies, caries, surface bacteria on the tissue of the parodontium or bacteria located in the tissue of the parodontium.

These are the most frequently occurring indications for afflictions of the teeth, which all can be diagnosed and also treated therapeutically using 5-amino levulinic acid or one of its derivatives.

Parodontopathies are inflammatory (>90%) degenerative (up to 4%) and hyperplastic (about 1%) diseases of the marginal parodontium multifactorial aethiology. Parodontitis is understood as an inflammation of the parodontium. Parodontosis is a degenerative form of parodontopathy with shrinkage of the marginal parodontium caused by primary regressive, noninflammatory processes under the formation of pockets and the loosening of the teeth.

Depending on the progression and type of bacterial affliction, the bacteria is located on the surface of the tissue of the parodontium or has penetrated into the tissue. The photodynamic diagnosis now possible allows a localization of the afflicted areas in a first step and thus opens up thus the possibility of subsequently treating these areas in a direct photodynamic therapy.

In a further configuration of the present invention, the 5-amino levulinic acid or one of its derivatives is used in a carrier substance, selected from the group consisting of hydrogels, in particular alginate gel, an oil and water emulsion or a buffer solution having a pH of 5 to 6.

These substances are very compatible and allow a topical application, such that the precursor of the photo-sensitizer can be held on location with the carrier substance sufficiently long, where it can then diffuse into the tissue or in the afflicted area. This procedure may require several hours, so that the danger exists that the precursor is washed away by saliva in the mouth. The carrier substance in the form of the above embodiment prevents such a washing by saliva. An oral administration is also possible or a systemic administration, which makes a local application of the precursor with the carrier unnecessary.

In a further embodiment of the present invention, an ester is employed as a derivative of the 5-amino levulinic acid. The use of esters has the advantage that they are chemically more stable than the 5-amino levulinic acid itself. It should be considered that not only saliva but also various enzymes are always present in the mouth, which could lead to rapid dissociation reactions of the 5-amino levulinic acid. A further advantage of an ester is that it provides a substantially higher penetration into the tissue due to better lipophylic properties than does the 5-amino levulinic acid. In the area of dental care, this offers the possibility of a rapid diagnosis and/or therapy after application of the precursor to the photosensitizer. For example, the patient can be diagnosed after application within a relatively short waiting time. In addition, substantially lower concentrations of esters can be used because of the faster penetration, so that possible side effects can be reduced or suppressed. For example, where an acid concentration of 160–200 mmol would be used, in comparison a concentration of 4–16 mmol of hexyl ester would be sufficient.

A further more important advantage of esters, in particular methyl ester, ethyl ester and particularly significant hexyl ester, is that they produce a substantially stronger and more homogeneous fluorescence. For example, the hexyl ester of 5-amino levulinic acid causes a fluorescence 50 times stronger than the acid. In addition, the hexyl ester has a higher tissue penetration compared to the acid by a factor of 2. This then opens the way in the special area of dental care that a patient comes into the dental clinic, the pharmaceutical preparation containing the precursor for the photo-sensitizer is applied and the diagnosis is made or a therapy is begun after only a short time. This also considerably simplifies the practical use or the acceptance by patients, the so-called compliance.

In a further embodiment of the present invention, the carrier substance and the precursor of the photo-sensitizer are mixed shortly before application. This feature is of advantage especially when the ester is used as a chemically stable substance. The two components, precursor as such and the carrier substance, can be stably stored over longer periods and a suitable mixture is prepared shortly before application, which is then applied.

The apparatus for administration comprises two chambers for this purpose, in which these substances are received, and a mechanism for mixing the two substances just before application. The mixture can then be supplied directly to the location on the parodontium or on the teeth via the canula.

The precursor, e.g. 5-amino levulinic acid, and the carrier substance, e.g. alginate, can be contained as powder in one chamber. A buffer solution can be contained in the second chamber. The pharmaceutical preparation resulting from mixing has the form of a gel.

An advantageous embodiment of the light application unit comprises two wave guides. The feature has a considerable advantage that one wave guide can be inserted into the tooth pocket between the tooth and the gum tissue and a further guide can be placed from the outside onto the gum. The excitation light can be specifically directed from two sides onto the afflicted area of the gum. In particular, when the bacteria has already deeply penetrated into the gum, the two-sided irradiation of the afflicted area is optimal, in particular for photodynamic therapy, so that successful therapy can be achieved after short intensive irradiation times.

In a further embodiment of the present invention, the two wave guides run adjacently, wherein an emitting end face of one wave guide extends beyond the emitting end face of the other guide in distal direction. This embodiment has the advantage that the further extending wave guide can initially be directly inserted into a pocket between the gum and the tooth and then the other wave guide can be placed from the outside onto the gum. Or, if the pocket is not deep, precisely the opposite. The further extending guide can be placed over a large surface area on the outside of the gum and the shorter guide inserted only into the relatively small pocket.

In a further embodiment of the present invention, one wave guide is axially shiftable relative to the other wave guide. The feature has the advantage that the mentioned handling is improved in its variability. This allows the dentist an optimal adaptation to the respective conditions and an optimal adaptation to the geometry to the parodontium of the patient, in particular in anomalous situations and problematic dispositions of the teeth.

In a further embodiment of the present invention, the shiftable wave guide is fed through a tubular channel. The feature has the advantage that the shiftable and sometimes relatively thin wave guide can be exactly guided over a long distance, whose movement can be reliably controlled.

In a further embodiment of the present invention, the tubular channel is configured for supplying media. This feature has the considerable advantage that flushing or suctioning or relieving a gas can be performed through the channel to support the therapy. Cool compressed air contributes to the subjective relief of pain in PDT. An acceleration of the PDT effect is produced by supplying oxygen. It is also possible to administer the pharmaceutical preparation containing the precursor through this channel.

In a further embodiment of the present invention, the element arranged in the light beam is a filter. In particular, various filters can be disposed in the light path. One of the filters transmits in the region of the excitation spectrum of the employed photo-sensitizer, thus induces fluorescence excitation in the inflamed tissue for photodynamic diagnosis. When the second filter transmits at least in the region of fluorescence emission, it then is used in photodynamic therapy of the tissue, especially in the region of the inflamed tissue.

In a further embodiment of the present invention, a third filter is provided which can be mounted in the optical path of the operator to the location on the parodontium being treated, which blocks fluorescence excitation light, however passes the fluorescence emissions. This feature has the advantage that the operating person can simply detect the fluorescence which characterizes the tissue.

In a further embodiment of the present invention, a wave guide is configured as a plurality of light transmitting individual fibers. The feature has the advantage that the light can be transmitted through the curvature without problem. The active diameter of the individual fibers lies in the range of 20 to 400 $\mu$m. By melt-fusing the individual fibers to a type of glass rod, a sufficiently rigid structure is formed, so that no additional mantle is necessary. In addition, a sufficient biocompatibility is achieved and the structure can be sterilized for example in an autoclave.

In a further embodiment of the present invention, the wave guide consists of a single light transmitting fiber. This feature has advantages in construction. Optionally, for handling purposes this wave guide must be reinforced with a mantle tube to achieve sufficient rigidity.

The individual fiber has an active diameter in the range of about 200 to about 2000 $\mu$m. This small calibration wave guide has the advantage that irradiation can take place directly in the tooth pocket. The optical fiber can be a glass fiber, synthetic fiber, quartz fiber or also a liquid wave guide.

In a further embodiment of the present invention, a further wave guide is provided which transmits light from the irradiated area in the proximal direction. This further wave guide can be part of a multi-fiber wave guide, which actually transmits light in the distal direction. This feature has the advantage that the return light can be used for detection of the fluorescence and thus also used for dosing in the PDT procedure. The determination of light intensity decay from the photo-sensitizer can be used in the PDD mode for dosing or for time control in the PDT procedure.

Depending on the configuration of the wave guide, not only light but also an entire image can be returned with appropriate individual fibers, which is then supplied to a image detection or image processing system, for example a miniaturized CCD camera.

In a further embodiment of the present invention, the light guided from the proximal end by the further wave guide is supplied to an evaluation unit. The evaluation unit is preferably a spectral analysis unit, a camera or a spectrally selective, sensitive photo element. This feature has the advantage that the returned light or image can be detected and quantified by a corresponding evaluation unit and for example the local information on the light decay process can be monitored. With this, the photodynamic treatment can be controlled and calculated.

In a further embodiment of the present invention, the wave guide is provided with a spacer at the distal end. The feature has the advantage that a constant radiation intensity can be achieved, thus providing a better dosing in the photodynamic therapy.

In a further embodiment of the present invention, the wave guide comprises a diffuser at the distal end. The diffuser can be configured as a spherical convex expansion of the distal end of the wave guide, or the diffuser can be formed as a light permeable material with properties for controlling optical transmission. Alternatively, the diffuser can be configured as an inflatable balloon, arranged at the distal end of the wave guide, which can be inflated via a channel.

This feature has the advantage that the relatively colminated light directly emitted from the relatively small face of the end of the wave guide can be uniformly distributed over a larger area, so that uniform treatment conditions are established for example in the entire tooth pocket in which such a wave guide is inserted.

In a further embodiment of the present invention, an ultrasound transmission element is provided through which ultrasound can be transmitted to the distal end. The feature has the advantage that the parallel application of ultrasound (e.g. 20 KHz to 3 MHz) can lead to an enhancement of the effect in photodynamic therapy and therefore to a more rapid inactivation of bacteria. It has been found that the penetration depth of the precursor of the photo-sensitizer is increased with the ultrasound effect and thus the desired depth effect in the treatment is improved.

In a further embodiment of the present invention, an ultrasound excitation unit is provided which is coupled to the ultrasound element. The feature has the advantage that the light application unit itself is also designed for ultrasound generation.

In a further embodiment of the present invention, the wave guide is configured as an ultrasound transmission element. The feature has the advantage that both light and ultrasound are transmitted in constructively simple manner, namely with one and the same element, namely the wave guide. For example, a piezo-electric drive can be attached to the wave guide, in particular a quartz wave guide.

In a further embodiment of the present invention, the light source has a large blue component in the range of about 400 nm (±20 nm). The feature has the advantage that one lies in the excitation range for fluorescence of the protoporphyrine IX produced by the precursor, thus one is especially adapted to this range.

In a further embodiment of the present invention, the light source comprises a xenon discharge lamp. The feature has the advantage that the light source provides a large blue component, a high radiation intensity and a relatively small focal spot. With this, a greater light penetration depth is possible in therapy.

In a further embodiment of the present invention, the light application unit comprises a housing with a pistol-like handle, from which a tubular section extends in which the wave guide is disposed. The feature has the advantage that handling is possible with one hand in ergonomic manner.

In a further embodiment of the present invention, the tubular section can be coupled to the housing and is removable from the housing. The feature has the advantage that different wave guides, i.e. different dimensions such as diameter, length and curvature can be simply coupled depending on the application.

An additional advantage is when the wave guide and the tubular section are formed to be conical in at least one section, namely to the distal end, where a tampered distal tip of the wave guide is formed, which can be better guided to the parodontium. The cone also causes a type of focusing and an increased distal irradiation angle with the effect of a more homogeneous illumination.

In a further embodiment of the present invention, the third filter is mounted on the tube section and preferably arranged there to be shiftable and pivotal. The feature has the advantage that a simple and flexible positioning of the observation filter can be carried out to provide favorable observation and visual conditions for the respective handling position.

In a further embodiment of the present invention, a canula is provided through which a pharmaceutical preparation can be administered. The feature has the advantage that the unit provided for light application is configured as a multi-functional device, i.e. can also be employed for administration of the pharmaceutical preparation.

It will be understood that the above-mentioned features and those to be described below are applicable not only in the given combinations, but also in other combinations or taken alone without departing from the scope of the present invention.

BRIEF DESCRIPTION OF THE DRAWINGS

The invention is described in more detail below in terms of selected embodiments in conjunction with the appended drawings.

FIG. 3 shows a variation of a removable tube section of the light application unit.

FIG. 4 shows an illustration corresponding to that of FIG. 3 of a further variation of a tube section for applying the pharmaceutical preparation.

DETAILED DESCRIPTION OF PREFERRED EMBODIMENTS

Figure 1:
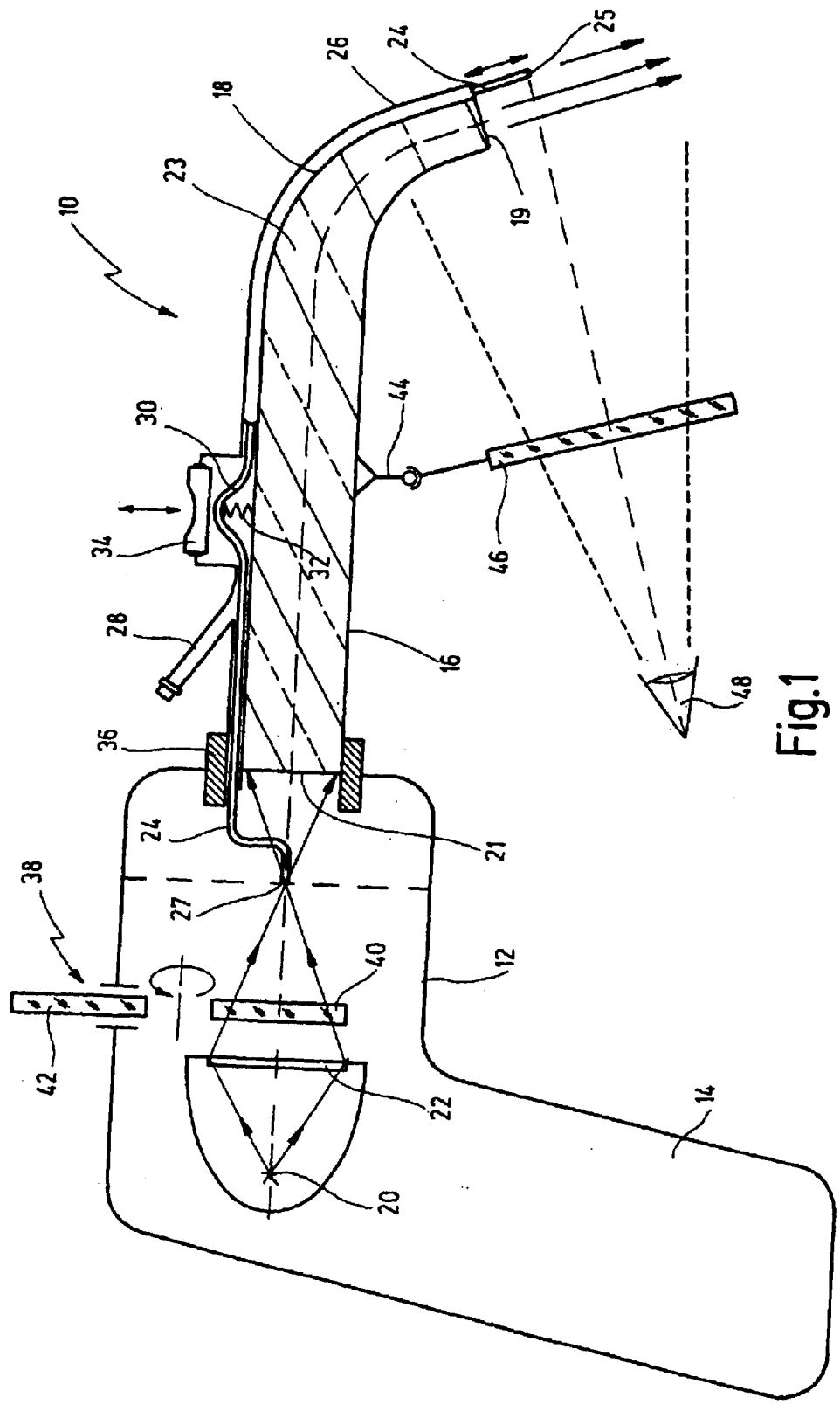
FIG. 1 shows a highly schematical side view of a light application unit according to the invention.

A light application unit is shown in FIG. 1 and indicated with the numeral 10. The light application unit 10 comprises a housing 12 from which a pistol-like handle 14 projects at an angle at the proximal end. A tube section 16 extends from the housing 12 at the end opposing the handle 16, which goes over into a curved section 18 at the distal end, which is slightly conically tampered toward its distal end 19.

The housing 12 includes a light source 20 and a focusing unit 22 which focuses light from the light source 20 onto the proximal end 21 of a first wave guide 23. Depending on the configuration of the light application unit 10, the light source 20 is powered by an energy source arranged in the housing 12 or is connected to an external energy source via a cable.

The first wave guide 23 itself is a bundled glass fiber formed of a plurality of individual glass fibers adhered to one another. The bundled glass fibers form a rigid body in a distal region for handling, said region extends within the tube section. The first wave guide 23 fills the inner space of the tube section 16. The conical tamper towards the distal end 19 for emitting excitation light provides a type of focusing and also an increase in the irradiation angle toward the distal end, which leads to a more homogeneous illumination.

A second wave guide 24 is arranged in a channel 26 provided in the interior of the tube section 16. The second wave guide 24 can also be composed of a rigid but elastic bundle of individual fibers or be one individual rigid but elastic fiber. A connector 28 extends from the channel 26 through which the channel 26 can be supplied with further media for example oxygen or a fluid. These media are passed through the free lumen between the second wave guide 24 and the inner side of the channel 26. A proximal end 27 of the second wave guide 24 lies in the focal range of the focusing unit and light is introduced there into this wave guide.

The second wave guide 24 is provided with a hump 30 in the straight section of the tube section 16, under which a compression spring 32 is arranged. The top of the hump 30 lies at the underside of a button 34, which is disposed in a housing, not described in detail here. The opposite side of the spring 32 is supported on the outer side of the tube section 16.

At the distal end, the second wave guide 24 extends beyond the channel 26. Light is emitted from the outer end 25 of the second wave guide 24, which has been introduced into the proximal end of the second wave guide 24 via the focusing unit 22. When the button 34 is depressed, the hump 30 becomes flatter and consequently the second wave guide 24 is pushed further out of the tube section 16. When the button 34 is released, the spring 32 urges the button 34 upwardly and the second wave guide 24 is retracted.

A coupling is indicated schematically with the numeral 36 through which the tube section 16 is coupled to the housing 12. The coupling 36 normally consists of a bayonet coupling. Thus it is possible to remove the tube section 16 from the housing 12 and to recouple this section or another tube section in a simple release and coupling procedure, as will be described below. The coupling can also be provided as a plug coupling or as a screw coupling.

Elements 38 are arranged in the housing which can be disposed in the beam path between the light source 20 and the wave guides 23, 24. These elements comprise a first filter 40 as well as a second filter 42 which can be rotated into and out of the beam path by a mechanism, not discussed in more detail.

The first filter 40 is configured such that it transmits in the region of the excitation spectrum of the photo-sensitizer. The second filter 42 is configured such that it transmits in the region of fluorescence emission of the photo-sensitizer. In the illustrated mode, the first filter 40 is in place and passes substantially only the fluorescence excitation light. In this position, the light application unit 10 operates particularly for photodynamic diagnosis.

A third filter 46 is arranged on the underside in the illustration of FIG. 1 on the outside of the tube section 16 via a support 44. The third filter 46 is pivotal and also shiftable in the longitudinal direction of the tube section 16 via the support 44.

This third filter 46 is to be placed between the eye 48 of the person handling the light application unit 10 and the area irradiated by the wave guide 23. This third filter 46 is configured such that the excitation light passing through the first filter 40 and through the wave guide 23 is blocked, the fluorescence light however is transmitted through the filter 46, where a detection of the fluorescence of the irradiated area characterizing the tissue is possible.

Figure 2:
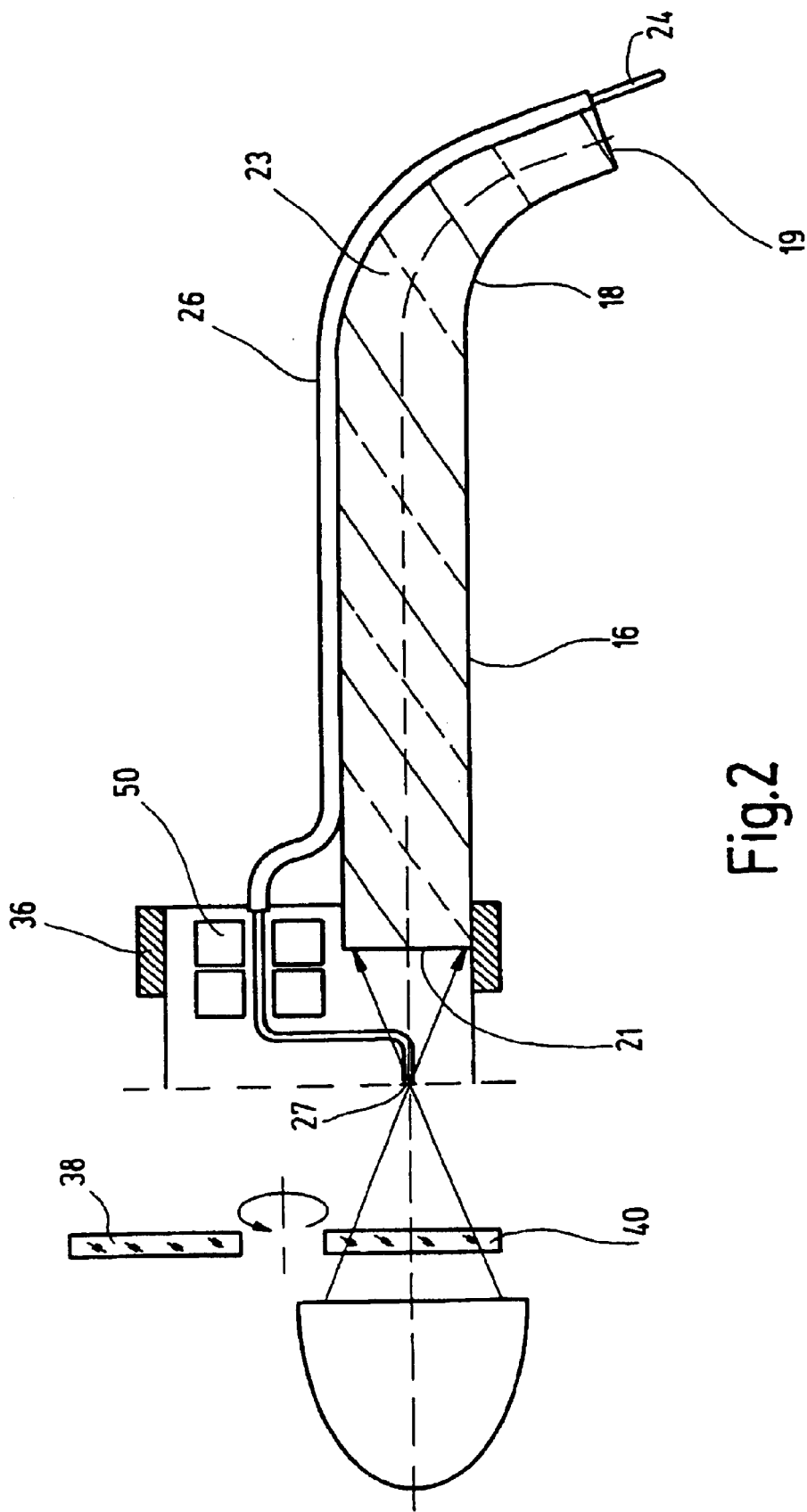
FIG. 2 shows a greatly simplified schematic side view of a further variation with an ultrasound generation unit.

In the variation of the light application unit illustrated in FIG. 2, the same reference numerals are used for the same components as in FIG. 1. An ultrasound excitation unit 50 is provided at the proximal end region of the second wave guide 24, which surrounds this part of the wave guide 24. The wave guide 24 in this case provides light transmission from the the light source 20, and also transmission of ultrasound coupled into the proximal end of the wave guide 24. In this case, the second wave guide 24 in advantageous manner consists of quartz glass.

As mentioned above, the tube section 16 is removable in a simple procedure from the housing 12 via the coupling 36 and can be reconnected thereto. In the variation of the tube section 16 shown in FIG. 3, a diffuser 52 is arranged at the outer distal end of the second wave guide 24. This diffuser 52 provides a uniform distribution of the light exiting from the relatively small end side surface, so that a uniform radiation is achieved about a large region.

When the diffuser 52 is formed to be relatively stiff, it can also serve as a spacer 54. In one embodiment, the diffuser 52 is formed as a balloon 53 in communication with the channel 26 so that a medium can be supplied to inflate the balloon, thereby generating a relatively large radiation surface on site.

In the variation in FIG. 4, the tube section 16 comprises a canula 56 at its center being connected at the proximal end with a container 58. The container 58 comprises a first chamber 62 and a second chamber 64. 5-amino levulinic acid or one of its derivatives is contained in the first chamber 62, for example hexyl ester and the alginate gel, each in powder form. A carrier substance, for example a buffer solution is contained in the second chamber 64. A mechanism 65 serves to mix the substances contained in the two chambers 62, 64 and then inject the mixture into the canula 56. The buffer solution provides a pH of 5–6. The alginate gel represents a carrier substance after mixing.

When the tube section 16 illustrated in FIG. 4 is coupled to the housing 12, the light application unit 10 can also be used as an apparatus 60 for administering the photo-sensitizer. If this is not desired, this apparatus can be configured as a separate apparatus for administering the pharmaceutical preparation. The mechanism 65 then is formed for example as a plunger which destroys the separating wall 63 between the chamber 62, 63 and mixes their contents and then injects the same through the canula 56.

Figure 5:
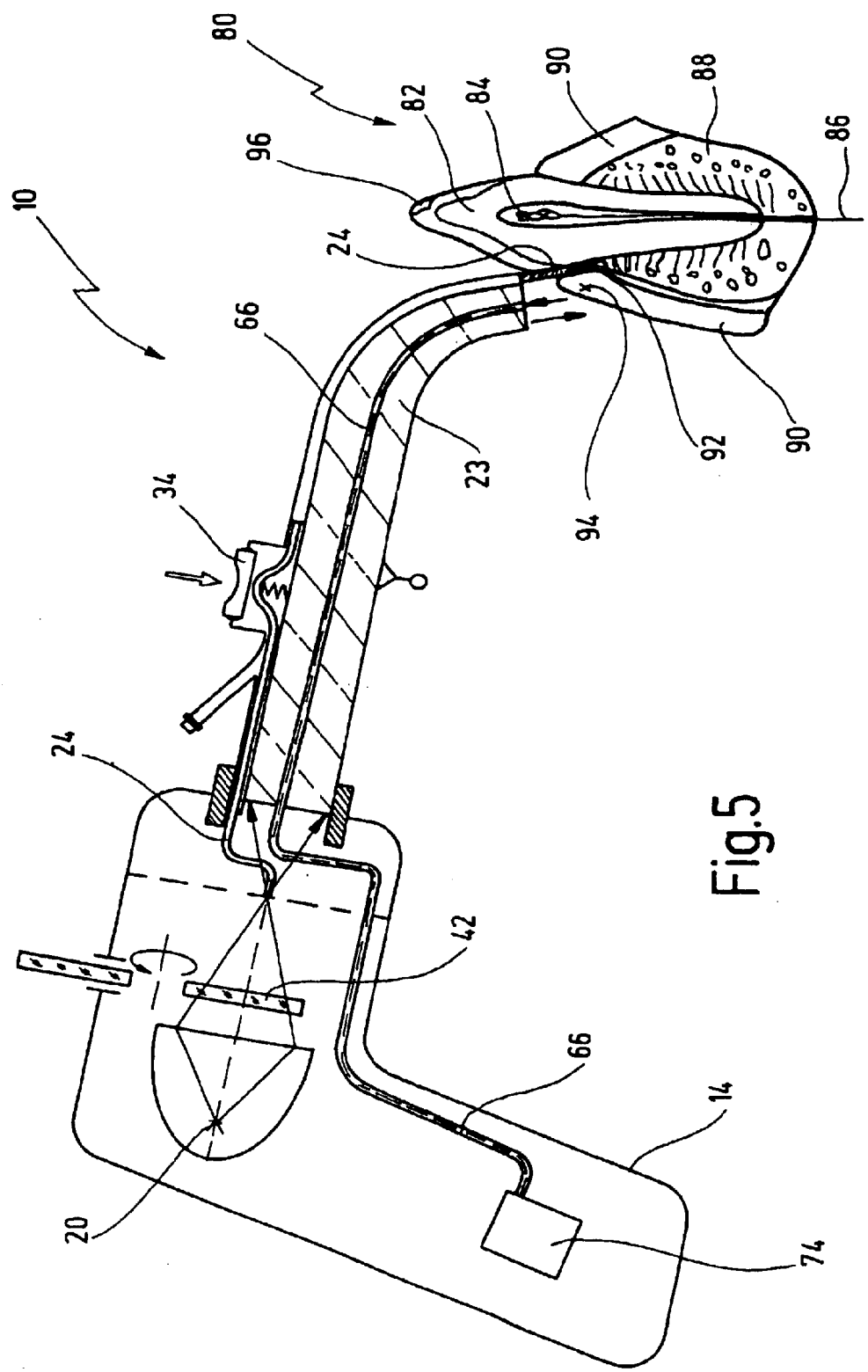
FIG. 5 shows a light application unit during a photodynamic therapy on a parodontium.

A use of a light application unit 10 for therapy is indicated in FIG. 5, where a variation is shown with the first wave guide 23 configured as a multi-fiber wave guide with a part, i.e. a few optical fibers are used to transmit light from the distal end to the proximal end. This wave guide 66 is connected to an evaluation unit 74 arranged in the handle 14, which can also be arranged externally, where a corresponding light transmitting connection can be provided.

A portion of the human parodontium 80 is shown in FIG. 5. It includes a tooth 82 having a nerve 86 located in the interior 84 of the tooth. The lower end of the tooth 82 sits in the jawbone 88 and is surrounded by the gums 90. In the course of a disease, a pocket 92 has formed between the outer side of the tooth 82 and the gums 90.

A mixture of 5-amino levuline acid hexyl ester and alginate gel has been previously applied into this pocket 92 and the waiting time is about two hours. The alginate gel resulted from the alginate powder and the buffer solution. In the meantime, the precursor of the photo-sensitizer has penetrated into the interior region 94 of the gums due to the high penetration speed and the high penetration depth of the ester. This has led to an accumulation of the photo-sensitizer protoporphyrine IX in the afflicted region.

The light application unit 10 is then placed against the parodontium 80, such that the shiftable second wave guide 24 or its distal end extending from the tube section 16 is inserted into the pocket 92. This procedure is simplified through the shifting capability. The first wave guide 23 directs light to the outer side of the gums 90. Subsequently, the light source 20 is activated, which preferably is a xenon discharge lamp emitting in the blue region. The second filter 42 transmits in the region of this excitation spectrum of the photo-sensitizer and this light is passed via the first wave guide 23 and the second wave guide 24 to the parodontium 80. The interior region 94 undergoes an optimal therapeutic treatment due to the two-sided radiation. A few of the wave guides 66 of the first wave guide 23 transmits fluorescence light emitted by the photo-sensitizer from the distal end back to the proximal end. These wave guides 66 are connected to an evaluation unit 74.

During the therapy, this evaluation unit 74 detects the decay of fluorescence emission and thus the course of the destruction of the afflicted tissue through the photodynamic therapy. Filters are provided to filter out the excitation light which is also returned, the filters only transmitting fluorescence light.

In FIG. 5, a region of the tooth 82 afflicted with caries is indicated with the numeral 96. As can be seen, this region 96 can also be diagnosed as well as subjected to therapy with the light application unit 10. The described light application unit is also utilizable in principle for other photo-sensitizers which show the same phenomenon on the parodontium and the teeth.

What is claimed is:

1. A light application unit for photodynamic diagnosis and for a photodynamic therapy of non-malignant diseases of a parodontium and of a tooth of a living being, comprising:

a light source for generating a light with a wavelength spectrum lying at least in the visible region;

a focusing unit for said light;

at least one element arrangeable in a light beam path of said light generated by said light source, said at least one element altering a spectral property of said light; and two wave guides for transmitting said light emitted from said light source to a distal emitting end of said two wave guides, said two wave guides positioned adjacent to each other, wherein an emitting end face of one of said two wave guides projects in a distal region beyond an emitting end face of the other of said two wave guides, and wherein one of said wave guides is arranged to be alternately axially extendable and retractable relative to the other wave guide, said two wave guides are configured rigidly in at least a distal region for handling, and said two wave guides being curved in a distal end section thereof.

2. The light application unit of claim 1, wherein two wave guides are provided.

3. The light application unit of claim 2, wherein said two wave guides run adjacent to another, and wherein an emitting end face of one of said two wave guides projects in a distal direction beyond an emitting end face of the other of said two wave guides.

4. The light application unit of claim 3, wherein one of said two wave guides is arranged to be axially shiftable relative to the other wave guide.

5. The light application unit of claim 4, wherein said shiftable wave guide is disposed within a tubular channel.

6. The light application unit of claim 5, wherein said tubular channel is configured for additionally supplying media.

7. The light application unit of claim 1, wherein said at least one element arrangeable in said light beam path is configured as a filter.

8. The light application unit of claim 7, wherein different filters are arranged to be brought into or out of said light beam path.

9. The light application unit of claim 1, wherein a filter is provided which can be disposed in a view direction of an operator handling said light application unit and a treatment area of said parodontium, wherein said filter blocks a fluorescence excitation light emitted by said light source, however transmits fluorescence emission light, emitted from said parodontium and said tooth of said living being illuminated by said light application unit.

10. The light application unit of claim 1, wherein said at least one wave guide is composed of a plurality of light transmitting individual fibers.

11. The light application unit of claim 1, wherein said at least one wave guide is formed of a single light transmitting fiber.

12. The light application unit of claim 1, wherein a further wave guide is provided, which transmits light in a proximal direction from a region irradiated by said light application unit.

13. The light application unit of claim 12, wherein said further wave guide is a part of a multi-fiber wave guide transmitting light to a distal direction.

14. The light application unit of claim 13, wherein said light transmitted proximally by said further wave guide is supplied to an evaluation unit.

15. The light application unit of claim 14, wherein said evaluation unit comprises at least one of a spectral analysis unit, a camera, a spectrally selective sensitive photo element.

16. The light application unit of claim 1, wherein one wave guide is provided with a bulbous spacer at a distal end thereof.

17. The light application unit of claim 1, wherein said at least one wave guide is provided with a diffuser at a distal end thereof.

18. The light application unit of claim 17, wherein said diffuser is configured as a spherical convex expansion of said distal end of said wave guide.

19. The light application unit of claim 18, wherein said diffuser is configured of a light-permeable material with optically controllable properties.

20. The light application unit of claim 19, wherein said diffuser is formed as an inflatable balloon arranged at said distal end of said wave guide, which balloon is inflatable via a channel.

21. The light application unit of claim 1, wherein an ultrasound transmission element is provided, through which ultrasound can be transmitted to said distal end of said wave guide.

22. The light application unit of claim 21, wherein an ultrasound excitation unit is provided to be coupled with said ultrasound transmission element.

23. The light application unit of claim 22, wherein said wave guide is configured as an element for transmitting said ultrasound.

24. The light application unit of claim 1, wherein said light source has a large blue component in the region of 400 nm.

25. The light application unit of claim 24, wherein said light source comprises a xenon discharge lamp.

26. The light application unit of claim 1, further comprising a housing is provided having a pistol-like handle, and a tube section extending from said housing, one wave guide being disposed within said tube section.

27. The light application unit of claim 26, wherein said tube section is configured to be coupled to said housing and can be removed from said housing.

28. The light application unit of claim 27, wherein said tube section is formed to taper conically over at least one portion of its length towards said distal end of said wave guide.

29. The light application unit of claim 28, further comprising a filter disposed so as to filter fluorescence radiation emitted from a treatment area of said parodontium, said filter mounted to said tube section.

30. The application unit of claim 29, wherein said filter mounted to said tube section is mounted to be shiftable and pivotal.

31. The light application unit of claim 1, wherein a canula is provided, through which canula said pharmaceutical preparation can be applied to said living being.

32. The light application unit of claim 1, further comprising an apparatus for applying said pharmaceutical preparation to said living being for performing a photodynamic diagnosis and a photodynamic therapy, said apparatus comprising, at least two chambers, 5-amino levulinic acid or a derivative thereof is received in a first chamber, and a carrier substance for said compounds in said first chamber is present in a second chamber, a mechanism for connecting said two chambers and mixing the components contained within said two chambers shortly before applying said pharmaceutical preparation to said living being, and a canula for passing said pharmaceutical preparation to a tissue area of a parodontium or a tooth of said living being.

* * * * *